United States Patent [19]

Uchikawa et al

[11] Patent Number: 5,006,221

[45] Date of Patent: * Apr. 9, 1991

[54] OXYGEN CONCENTRATION-DETECTING APPARATUS

[75] Inventors: Akira Uchikawas; Satoshi Anbe; Masami Kawashima; Tatsumasa Yamda; Tadao Suwa, all of Isesaki, Japan

[73] Assignee: Japan Electronic Control Systems Co., Ltd., Isesaki, Japan

[*] Notice: The portion of the term of this patent subsequent to Sep. 27, 2005 has been disclaimed.

[21] Appl. No.: 313,890

[22] Filed: Feb. 23, 1989

[30] Foreign Application Priority Data

Mar. 1, 1988 [JP] Japan .................................. 63-45739

[51] Int. Cl.[5] .......................................... G01N 27/417
[52] U.S. Cl. ..................... 204/426; 204/424; 204/427; 204/428; 204/429
[58] Field of Search ............................ 204/19, 421–429

[56] References Cited

U.S. PATENT DOCUMENTS

| 4,199,425 | 4/1980 | Sinkevitch | 204/429 |
| 4,655,892 | 4/1987 | Satta et al. | 204/424 |
| 4,718,999 | 1/1988 | Suzuki et al. | 204/426 |
| 4,770,760 | 9/1988 | Noda et al. | 204/426 |
| 4,773,376 | 9/1988 | Uchikawa et al. | 123/489 |
| 4,795,544 | 1/1989 | Nishizawa et al. | 204/425 |

FOREIGN PATENT DOCUMENTS

| 58-120958 | 8/1983 | Japan . |
| 58-204365 | 11/1983 | Japan . |
| 59-203828 | 11/1984 | Japan . |
| 63-16258 | 1/1988 | Japan . |
| 63-113956 | 7/1988 | Japan . |

Primary Examiner—T. Tung
Attorney, Agent, or Firm—Foley & Lardner

[57] ABSTRACT

An oxygen gas concentration-detecting apparatus for use in an internal combustion engine comprising a plate-shaped substrate, a plate-shaped oxygen ion-conducting solid electrode for generating an electromotive force between a first surface contacted with air and a second surface contacted with an exhaust gas of the engine according to the difference between the concentrations of oxygen gases of the air and the exhaust gas, the solid electrode being laminated on the substrate, a pair of electrode members for taking out the electromotive force as a detection signal and a nitrogen oxide-reducing catalyst layer for promoting the reduction of nitrogen oxide arranged to cover the second surface of the oxygen ion-conducting solid electrode. By this apparatus, the concentration of oxygen gas inclusive of oxygen gas generated by reduction of nitrogen oxides can be precisely detected. The plate-shaped oxygen gas concentration-detecting apparatus enables to easily form a uniform catalyst reaction surface and to easily be heated so as to promote the stable reduction reaction of the nitrogen oxide-reducing catalyst layer.

18 Claims, 4 Drawing Sheets

OXYGEN CONCENTRATION-DETECTING APPARATUS

BACKGROUND OF THE INVENTION

1. Field of the Invention

The present invention relates to an apparatus for detecting the oxygen gas concentration in a sample gas. More particularly, the present invention relates to an apparatus attached to an exhaust tube of an internal combustion engine, which is suitable for detection of the oxygen gas concentration in the exhaust gas, which has a close relation to the air-fuel ratio of an air-fuel mixture supplied to the engine.

The apparatus may provide a feedback signal or the like for the feedback control of the air-fuel ratio, a fuel injection timing or an engine idle speed etc.

2. Description of the Related Art

As means for detecting the oxygen gas concentration in an exhaust gas of an internal combustion engine (hereinafter referred to as "oxygen sensor"), an apparatus disclosed in Japanese Patent Application Laid-Open Specification No. 203828/84 is known, and the main part for detecting the oxygen gas concentration in the oxygen sensor is known, for example, from Japanese Patent Application Laid-Open Specification No. 204365/83 or 16258/88.

Namely, the main part of the oxygen sensor has a plate type ceramic substrate composed mainly of zirconium oxide ($ZrO_2$), and parts of the inner and outer surfaces of the ceramic substrate are coated with a platinum (Pt) paste and the ceramic substrate is then calcined to form a pair of electrodes for taking out an electromotive force. Furthermore, platinum is vacuum-deposited on the outer surface of the ceramic substrate to form an oxidation catalyst layer for oxidizing unburnt components in the exhaust gas, such as CO and HC. Then, a metal oxide such as magnesium spinel is flame-sprayed on the oxidation catalyst layer to form a protecting layer for protecting the oxidation catalyst layer.

In this structure, the air is introduced as the stable reference gas onto the inner surface of the ceramic substrate, and the outer side of the ceramic substrate is exposed to an exhaust gas passage of the engine and is contacted with the exhaust gas of the engine. A voltage corresponding to the ratio of the oxygen gas concentration in air contacted with the inner surface of the ceramic substrate to the oxygen gas concentration in the exhaust gas contacted with the outer surface of the ceramic substrate is generated between the pair of electrodes, and the oxygen gas concentration in the exhaust gas is detected based on this voltage.

It is considered that the electromotive force effect is generated between the electrodes on the inner and outer surfaces of the ceramic substrate according to the following mechanism.

If calcia (CaO) or yttria ($Y_2O_3$) is added to zirconia ($ZrO_2$) known as a main component of a ceramic and the mixture is heated, calcia or yttria is included in the crystal and a lattice defect of the oxygen ion is formed, whereby zirconia is formed into a pure oxygen ion conductor in which the oxygen ion moves though either the electron or the hole hardly moves. If the oxygen partial pressure on one wall of densified zirconia is made different from the oxygen partial pressure on the other wall, it is only the oxygen ion $O^{2-}$ that can move, and as the result, an electromotive force is generated.

Incidentally, the oxidation catalyst layer of platinum promotes oxidation reactions of $CO + \frac{1}{2}O_2 \rightarrow CO_2$ and $HC + O_2 \rightarrow H_2O + CO_2$ between oxygen and carbon monoxide CO or hydrocarbon HC, and when combustion is carried out with a richer air-fuel mixture, CO or HC is conveniently reacted with low-concentration oxygen left in the air-fuel mixture to reduce the oxygen concentration almost to zero, whereby the oxygen concentration ratio between the inside and outside of the ceramic substrate is increased and a large electromotive force is generated. On the other hand, when combustion is carried out with a leaner air-fuel mixture since high-concentration oxygen and low-concentration CO and HC are present in the exhaust gas, even if oxygen reacts with CO and HC, $O_2$ still remains in a considerable amount, and the oxygen concentration ratio between the inside and outside of the ceramic substrate is low and no substantial voltage is produced.

Since the value of the electromotive force output from the oxygen sensor abruptly changes in the vicinity of the stoichiometric air-fuel ratio as pointed out above, by utilizing this phenomenon, it is judged whether or not the air-fuel ratio in an air-fuel mixture sucked in the engine is the stoichiometric air-fuel ratio. If the air-fuel ratio is richer than the stoichiometric air-fuel ratio, the amount of the fuel to be supplied into the engine is decreased or the amount of the intake air is increased, and if the air-fuel mixture is leaner than the stoichiometric air-fuel ratio, the amount of the fuel is increased or the amount of the intake air is decreased. Thus, feedback control of the air-fuel ratio is performed.

However, in the above-mentioned conventional oxygen sensor, the oxidation catalyst layer has no substantial effect of reducing nitrogen oxides $NO_x$, and therefore, the oxygen concentration in the exhaust gas is detected irrespectively of the concentration of nitrogen oxides $NO_2$.

Incidentally, nitrogen oxides $NO_x$ are formed by bonding of nitrogen $N_2$ in the air to oxygen in a high temperature atmosphere.

Namely, oxygen in $NO_x$ should be detected as oxygen concentration, which has not made any contribution to combustion, for detection of the air-fuel ratio, but this oxygen is not detected by the conventional oxygen sensor.

Accordingly, the detection value of the oxygen sensor is changed by the amount corresponding to the amount of oxygen which has reacted with nitrogen gas $N_2$ to form $NO_x$, and in the air-fuel ratio region where the detection value of the oxygen sensor is inverted, the apparent air-fuel ratio can not correspond to the actual air-fuel ratio and can not be stable by the change of amount of the $NO_x$ concentration even when the actual air-fuel ratio is constant.

Therefore, if feedback control of the air-fuel ratio is performed according to the detection result based on the air-fuel ratio in the inversion region of the oxygen sensor as the reference, the air-fuel ratio is erroneously controlled to an unpreferable level and there is a risk that oxidation reaction of nitrogen gas is advanced and nitrogen oxides $NO_x$ in the exhaust gas are excessive.

In general, a ternary catalyst for purging the exhaust gas, which is disposed in the exhaust gas passage in the engine, can simultaneously convert CO, HC and $NO_x$ efficiently when the air-fuel ratio is close to the stoichiometric air-fuel ratio, but if the air-fuel ratio is not controlled to a desired level i.e. the stoichiometric air-fuel ratio, the conversion of $NO_x$ is abruptly reduced and the amount of $NO_x$ discharged to the air present downstream of the ternary catalyst passage is drastically increased.

According to the conventional technique, so-called exhaust gas recycle (EGR) control for reducing nitrogen oxides $NO_x$ operates by recycling a part of the exhaust gas of the engine into the intake air and thus lowering the combustion temperature. However, the structure of this EGR control system is complicated because an EGR passage should be laid out and an EGR control valve or the like should be disposed in this passage, and this results in increase of the cost. Moreover, the combustion efficiency is reduced by introduction of the exhaust gas and the fuel expense is greatly increased.

Accordingly, if feedback control of the air-fuel ratio of the internal combustion engine is performed by the conventional inaccurate oxygen sensor, excessive discharge of nitrogen oxides $NO_x$ cannot be avoided, and in order to prevent nitrogen oxides $NO_x$ from being discharged to the outside, the EGR control system should be disposed in the internal combustion engine, which inevitably resides in the above-mentioned disadvantages.

In order to solve the above-described conventional problems, an oxygen sensor in which a nitrogen oxide-reducing catalyst layer for promoting the reduction reaction of nitrogen oxides has been provided as U.S. patent application Ser. No. 117,507 (U.S. Pat. No. 4,773,376) by the present applicant. Output characteristics of the proposed oxygen sensor keep stable even if the amount of the nitrogen oxides in the exhaust gas changes in case where the air-fuel ratio of the intake mixture maintains at a constant level.

However, since the oxygen sensor with the nitrogen oxides layers is constructed by using a test tube shaped ceramic tube having the top end closed and since the nitrogen oxide-reducing catalyst layer is formed on an outer curved surface of the ceramic tube, the thickness of the nitrogen oxide-reducing catalyst layer becomes inevitably uneven. Accordingly, the reaction is dense in the top end portion of the ceramic tube while the reaction is sparse on the side of the base end, and because of this difference of the reaction density, the degree of deterioration is made locally different in the oxygen sensor.

Further, it may be required for the proposed oxygen sensor with the nitrogen oxides layer to be heated so that the activation temperature thereof can be attained without a long time consumption when the exhaust gas is low and selection of kinds of reducing catalysts or the carrier for supporting the catalyst is not limited.

In case of the tube type oxygen sensing element, a rod-shaped heater may be placed in an inner cavity of a ceramic tube having the top end closed and an element is heated by this heater. However, in the structure where the heater as a separate body is inserted in the inner cavity of the ceramic tube, increase of the cost by the disposition of the heater cannot be avoided, and furthermore, since the heater is not directly contacted with the element (ceramic tube) but the element is heated through an air layer, the efficiency of the heating by the heater is low and a long time is required for heating the element at a temperature where the characteristics become stable.

OBJECT OF THE INVENTION

It is therefore a primary object of the present invention to provide a plate-shaped oxygen concentration-detecting apparatus for convenient use in an exhaust gas of an internal combustion engine in which oxidation reaction of nitrogen oxides $NO_x$ is further promoted to eliminate the above-mentioned disadvantages of the oxygen sensor without the nitrogen oxide-reducing function and the concentration of oxygen participated in combustion in the exhaust gas of the engine can be detected more accurately.

Another object of the present invention is to provide an plate-shaped oxygen concentration-detecting apparatus wherein the rising capacity and the stability of the catalyst temperature are improved at a low cost and a uniform reaction surface of the nitrogen oxide-reducing catalyst layer can be easily attained.

SUMMARY OF THE INVENTION

In accordance with the present invention, there is provided an oxygen concentration-detecting apparatus for an internal combustion engine which comprises a plate-shaped substrate, a plate-shaped oxygen ion-conducting solid electrolyte for generating an electromotive force between a first surface contacted with air and a second surface contacted with an exhaust gas of the engine according to the difference of the concentration of oxygen gas between the air and the exhaust gas, the oxygen ion-conducting solid electrolyte being laminated on an surface of substrate and the substrate restricting a cavity portion therebetween where air is introduced into a pair of electrode members formed at the first and second surfaces, respectively, of the oxygen ion-conducting solid electrolyte, to take out the electromotive force as a detection signal, and a nitrogen oxide-reducing catalyst layer for promoting the reduction of nitrogen oxide disposed on the second surface of the oxygen ion-conducting solid electrolyte and the electrode located on the second surface.

According to the oxygen concentration-detecting apparatus of the present invention, since reduction reaction of nitrogen oxides $NO_x$ is promoted by the reduction catalyst layer, the oxygen gas concentration on the second surface side of the oxygen ion-conducting solid electrolyte is increased by this reduction reaction. Therefore, the difference between the oxygen concentration on the open air side and the oxygen concentration on the exhaust gas side is proportionally decreased, and the electromotive force of the oxygen concentration-detecting apparatus is reduced and a richer value than in the conventional apparatus by the oxygen concentration of nitrogen oxides $NO_x$ is detected. Therefore, although the concentration of nitrogen oxides $NO_x$ changes by the engine driving condition, the air-fuel ratio is detected without any changes thereof and if feedback control of the air-fuel ratio is performed based on this detection result, the air-fuel ratio is controlled to, for example, a true stoichiometric air-fuel ratio.

The nitrogen oxide-reducing catalyst layer may comprise at least rhodium supported on titanium carrier so that even when the exhaust gas is in low temperature the reduction reaction of the nitrogen oxides can be carried out in the wide range of the temperature.

In accordance with the present invention further oxidation catalyst may be further comprised in the oxygen concentration-detecting apparatus in such a manner that the oxidation catalyst is included in the nitrogen oxides-reducing catalyst or the oxidation catalyst layer is located on each of surfaces of the nitrogen oxide-reducing layer, so as to enhance the detecting efficiency.

In accordance with the present invention the oxygen concentration-detecting apparatus may further comprises a protecting layer for protecting the nitrogen oxides-reducing catalyst layer from poisoning substances such as lead Pb and sulfur S whereby the durability is improved.

In the oxygen sensor having the above-mentioned structure, if a heater is integrally attached to the substrate to directly heat the element, the efficiency of the heating by the heater is higher than in the case where the heater is arranged as a separate body.

In the oxygen sensor of the present invention, since the plate-shaped oxygen ion-conducting solid electrolyte is laminated on the plate-shaped substrate, the thickness of the nitrogen oxide-reducing catalyst layer formed on the oxygen ion-conducting solid electrolyte (flat surface) on the side opposite to the substrate can be easily made uniform, and the irregularity of the reaction density on the reaction surface can be eliminated.

If the oxygen gas concentration-detecting apparatus of the present invention is used in combination with the conventional known air-fuel ratio feedback control means for an internal combustion engine, decrease of generation of $NO_x$ is precisely attained and a high control accuracy can be maintained.

The present invention will now be described hereinafter in detail with reference to the accompanied drawings.

DESCRIPTION OF THE PREFERRED EMBODIMENTS

Figure 1:
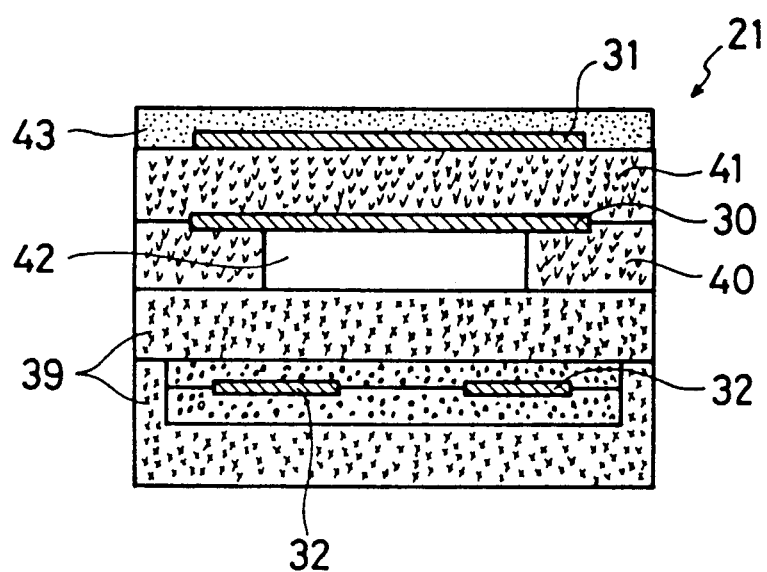
FIG. 1 is a sectional view of the sensor element portion of an oxygen sensor, which illustrates one embodiment of the present invention.
Figure 2:
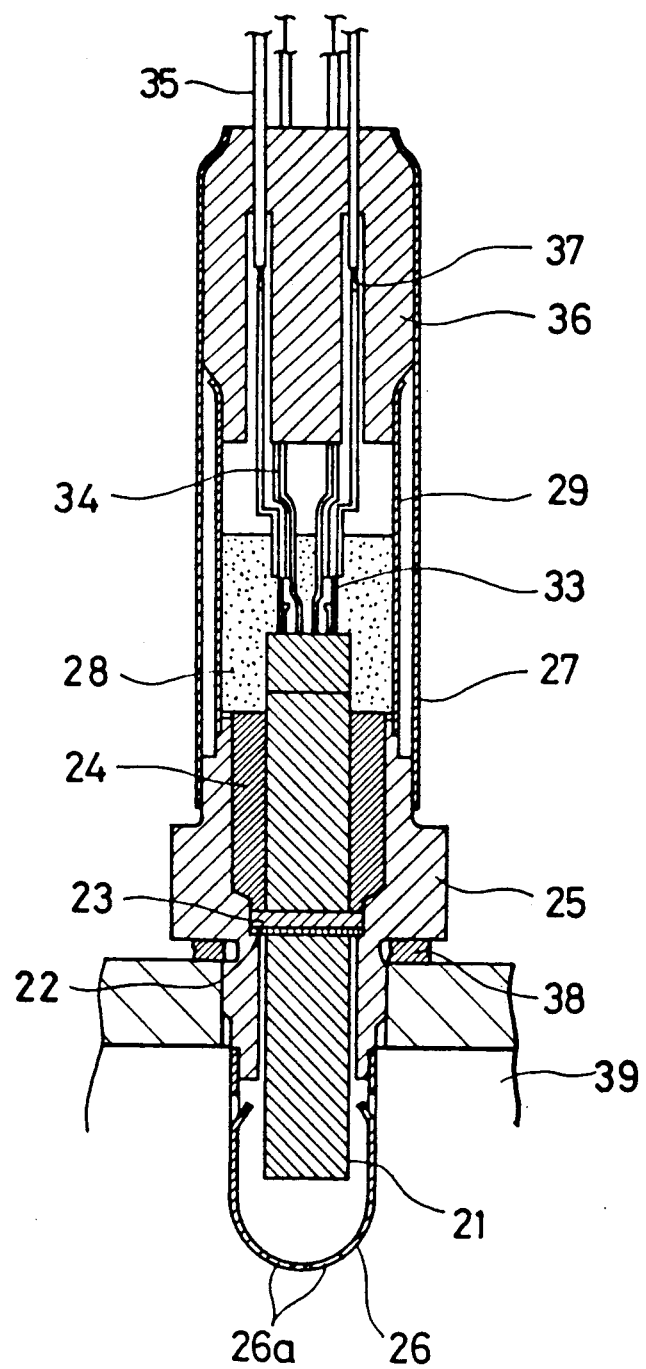
FIG. 2 is a sectional view illustrating the entire structure of the embodiment shown in FIG. 1.

In FIGS. 1 and 2, which illustrate one embodiment of the present invention, a sensor element portion 21 of an oxygen sensor described in detail hereinafter is held at an intermediate portion thereof by a holder 25 through two washers 22 and 23 and a glass layer 24. A cap-shaped protector 26 having a slit 26a in a peripheral wall thereof is fitted to the periphery of the top end of the holder 25 to cover the top end portion of the sensor element portion 21, and the periphery of the base end of the holder 25 is fitted to and carried on a cylindrical outer cap 27.

A base end of the sensor element portion 21 is held by a cylindrical inner cap 29 through a glass layer 28, and measurement electrodes 30 and 31 of the sensor element portion 21 and an electrode terminal 33 connected to a heater 32 are electrically connected to a lead harness 33 through a lead plate 34. Incidentally, reference numeral 36 represents a grommet for protecting a connecting portion 37 between the lead plate 34 and the lead harness 35, and reference numeral 38 represents a gasket. A general structure of the oxygen sensor is disclosed in detail in Japanese Utility Model Laid-Open Specification No. 113956/88.

The structure of the sensor element portion 21 will now be described in detail with reference to FIG. 1.

Referring to FIG. 1, the sensor element portion 21 comprises a plate-shaped oxygen ion-conducting solid electrolyte 41 composed of zirconia $ZrO_2$ or the like, which is laminated through a spacer 40 composed of alumina $Al_2O_3$, zirconia $ZrO_2$ or the like on a substrate 39 composed of alumina $Al_2O_3$ or the like, in which a heater (or heaters) 32 composed of platinum Pt or the like is integrally embedded.

A pair of measurement electrodes 30 and 31 composed of platinum Pt are formed on both the surfaces of the oxygen ion-conducting solid electrolyte 41 respectively, and the measurement electrode 30 on the side of the substrate 39 is exposed to a cavity portion 42 defined by a spacer 40. A nitrogen oxide-reducing catalyst layer 43 formed by supporting catalyst particles of rhodium Rh, ruthenium Ru, iridium Ir or osmium Os or platinum Pt capable of promoting the reduction reaction of nitrogen oxide $NO_x$ and platinum Pt capable of promoting the oxidation reaction of unburnt components such as HC and CO on a carrier is laminated on the outer surface of the measurement electrode 31 and the solid electrolyte 41. As the carrier, there can be used, for example, titanium oxide $TiO_2$, alumina $Al_2O_3$, silicon oxide $SiO_2$, magnesium oxide MgO and lanthanum oxide $La_2O_2$. The platinum Pt of oxidation catalyst may not be included in the reducing catalyst layer but the oxidation catalyst is effective to promote the nitrogen oxides reduction reaction.

The sensor element portion 21 is constructed so that air is introduced into the cavity portion 42, and by attaching the holder 25 to the exhaust pipe of the engine so that the side of the oxygen ion-conducting solid electrolyte 41 opposite to the substrate is exposed to the exhaust gas of the engine through the protector 26.

In the above-mentioned structure, when the nitrogen oxide $NO_x$ contained in the exhaust gas arrives at the nitrogen oxide-reducing catalyst layer 43, the nitrogen oxide-reducing catalyst layer 43 promotes the reactions of $NO_x$ with unburnt components CO and HC in the exhaust gas, represented by the following formulae:

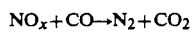

$$NO_x + CO \rightarrow N_2 + CO_2$$

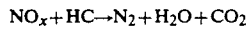

$$NO_x + HC \rightarrow N_2 + H_2O + CO_2$$

Accordingly, the unburnt components are consumed in the nitrogen oxide-reducing catalyst layer 43 and the amounts of the unburnt components bonded to oxygen $O_2$ are decreased. As the result, the concentration of oxygen $O_2$ is proportionally increased with increase of the concentration of the nitrogen oxide $NO_x$ in the exhaust gas, and hence, the electromotive force generated according to the difference between the concentration of oxygen $O_2$ in air, with which the measurement electrode 30 falls in contact, and the concentration of oxygen $O_2$ in the exhaust gas, with which the measurement electrode 31 falls in contact, changes according to the concentration of the nitrogen oxide $NO_x$ in the exhaust gas.

The conventional oxygen sensor afore-mentioned can not detect the oxygen concentration which is included in $NO_x$ component. Accordingly, assumed that the air-fuel ratio of the mixture sucked into the engine is stably constant, the conventional oxygen sensor detect only the varying oxygen concentration but the concentration in the $NQ_x$ component since the oxygen concentration in the exhaust gas changes according to the $NO_x$ concentration, which mis-judges as that the air-fuel ratio is not constant but changes by the $NO_x$ concentration.

However the oxygen sensor of the present invention can detect the oxygen concentration of oxygen in the exhaust gas as well as that of the $NO_x$ component. Therefore when the air-fuel ratio of the sucked intake mixture is constant the detected oxygen concentration which is close to the air-fuel ratio is also constant or stable with the result of showing the constant air-fuel ratio. This means that the oxygen sensor of the present invention can precisely detect the oxygen concentration without any harmful influences by the $NO_x$ concentration produced in the exhaust gas.

Figure 4:
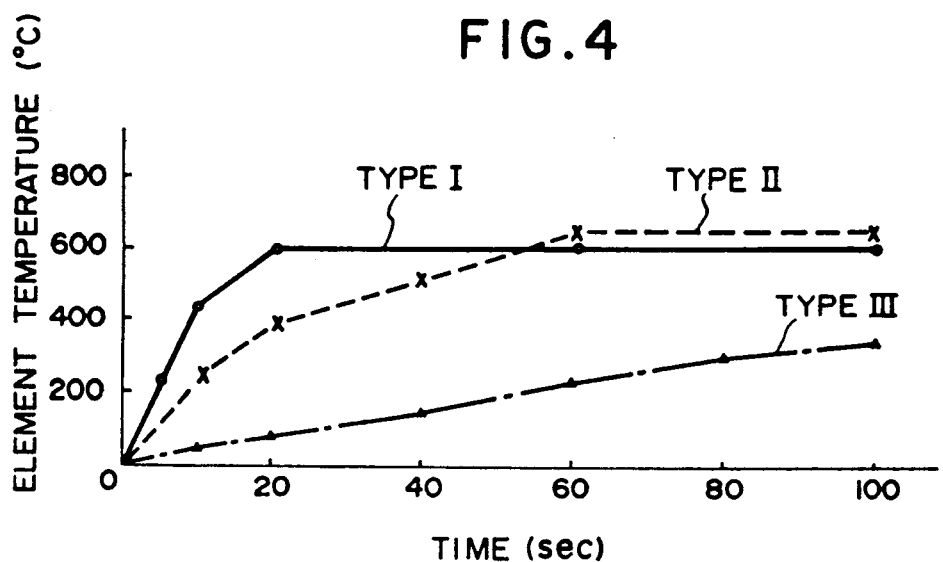
FIG. 4 is a graph illustrating the relation between the elapsing time and the temperature of the sensor element portions of the oxygen sensors.

If the heater 32 is integrally attached as in the present embodiment, the heating of the sensor element portion 21 by the heater 32 can be performed efficiently, and therefore, as shown in FIG. 4, the element temperature of the plate type sensor element portion (type I) according to the present invention can be promptly elevated to the activation temperature of the element from the state where the exhaust gas temperature is low, and simultaneously, the element temperature can be prevented from becoming unstable under the influence of the exhaust gas temperature. Accordingly, not only rhodium Rh and ruthenium Ru but also iridium Ir, osmium Os and platinum Pt can be used as the catalyst for reducing the nitrogen oxide $NO_x$, and as the carrier for these catalysts, there can be used not only titanium oxide $TiO_2$ and alumina $Al_2O_3$ but also silicon oxide $SiO_2$, magnesium oxide MgO and lanthanum oxide $La_2O_2$. For enabling comparison of the temperature characteristics of the type I, characteristics of a type II for a tube type oxygen sensor element with a heater and of a type III for a tube type oxygen sensor element without a heater are represented in FIG. 5.

Since the heater 32 is embedded in the substrate 39, increase of the number of constituent parts by attachment of the heater 32 can be avoided, and the heater 32 can be attached at a low cost.

Moreover, since the nitrogen oxide-reducing catalyst layer 43 is laminated on the plate-shaped oxygen ion-conducting solid electrolyte 41, formation of the nitrogen oxide-reducing catalyst layer 43 in a uniform thickness can be accomplished more easily than in the case where the catalyst layer 43 is formed on a tube or the like, and if the nitrogen oxide-reducing catalyst layer 43 is thus formed in a uniform thickness, the reduction reaction is uniformly advanced on the oxygen ion-conducting solid electrolyte 41.

Figure 5:
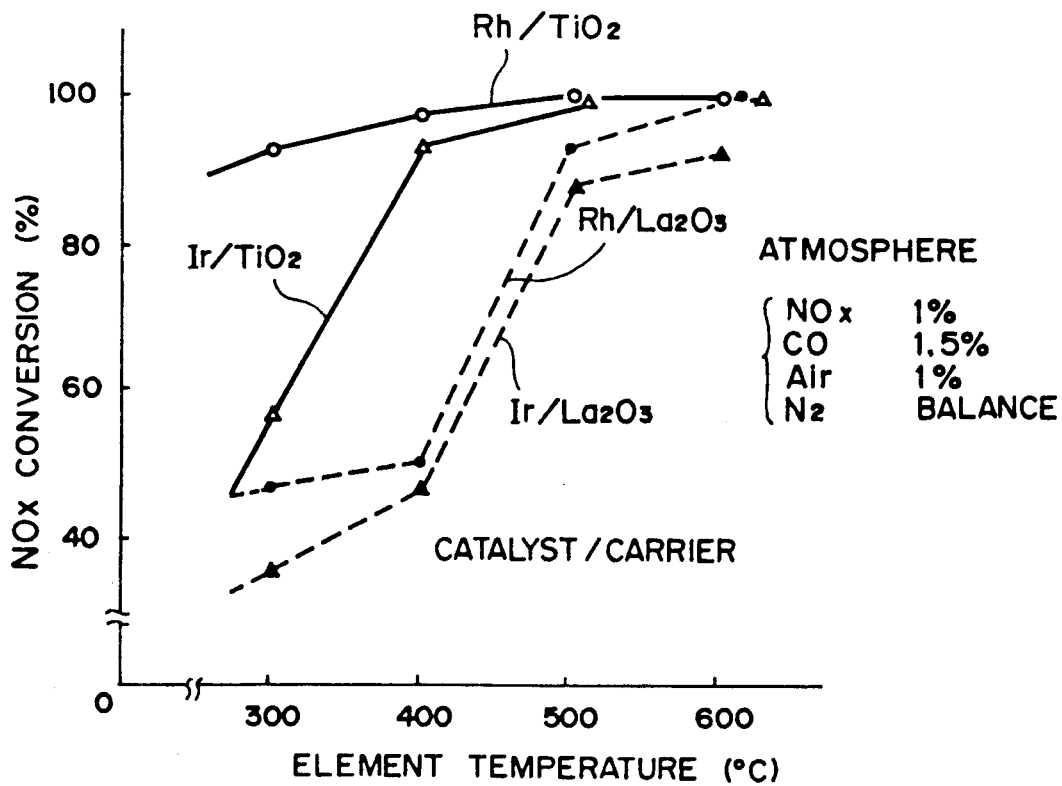
FIG. 5 is a graph illustrating the relation between the temperature of the sensor element portion and the conversion of $NO_x$ in oxygen sensors according to the present invention.

In the case where rhodium is used as the reduction catalyst and is supported on titanium oxide $TiO_2$ as the carrier, since the element is activated even at a relatively low element temperature (the conversion is high as shown in FIG. 5), a good workability can be obtained even if the heater 32 is not particularly arranged. However, also as shown in FIG. 6, in the case where iridium Ir is used as the reduction catalyst and is supported on titanium oxide $TiO_2$, the conversion is higher than the conversion attained when lanthanum oxide $La_2O_2$ is used as the carrier, but a sufficient conversion is not obtained if the element temperature is lower than about 400° C. Accordingly, in this case, it is preferred that the heater 32 be disposed.

Figure 3:
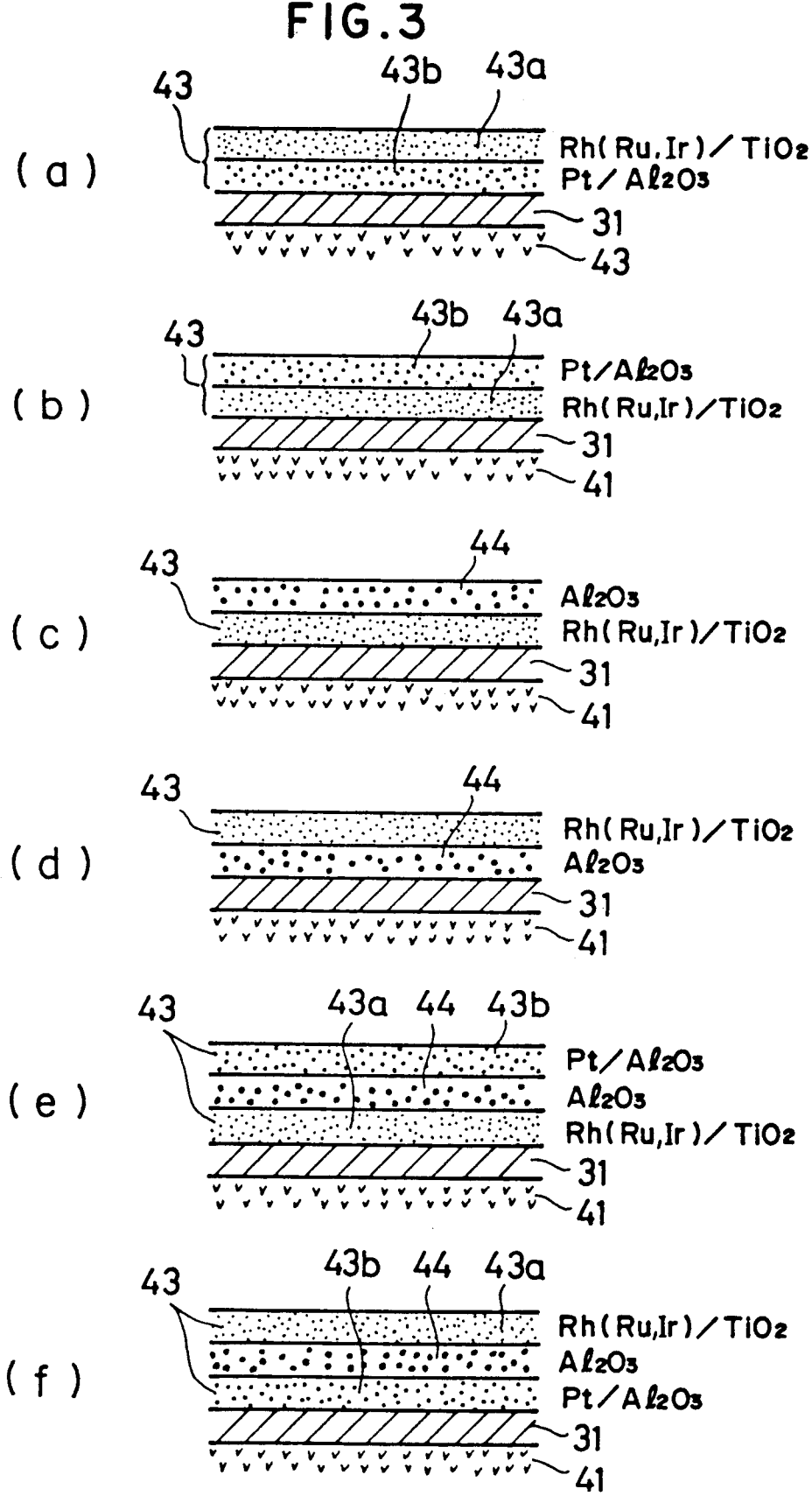
FIGS. 3(a) through 3(f) are sectional views showing sensor element portions of different oxygen sensors according to another embodiments of the present invention.

In order to improve the efficiency of the reduction reaction of the nitrogen oxide $NO_x$ in the nitrogen oxide-reducing catalyst layer 43, there may be adopted a method in accordance with the present invention in which a two-layer structure is given to the nitrogen oxide-reducing catalyst 43, as shown in FIGS. 3(a) and 3(b). In FIG. 3(a), an auxiliary catalyst layer (which is an oxidation catalyst layer) 43b comprising platinum Pt on alumina $Al_2O_3$ as the carrier is disposed between the outer electrode 31 and a reduction catalyst layer 43a comprising a reduction catalyst such as rhodium Rh, ruthenium Ru or iridium Ir, supported on titanium oxide $TiO_2$ as the carrier. By disposing the two layers system, the reduction reaction of the nitrogen oxide $NO_x$ is promoted more effectively.

In FIG. 3(b), the lamination order shown in FIG. 3(a) is reversed, and a layer comprising platinum Pt supported on alumina $Al_2O_3$ (auxiliary catalyst layer 43b) is formed on the outer side.

In the oxygen sensor comprising the nitrogen oxide-reducing catalyst layer 43, for improving the durability, a protecting layer 44 can be formed, as shown in FIGS. 3(c) through 3(f).

In FIG. 3(c), a layer of alumina $Al_2O_3$ is laminated as the protecting layer 44 on the outer side of the reduction catalyst layer 43 comprising a reduction catalyst such as rhodium Rh, ruthenium Ru, or iridium Ir, supported on titanium oxide $TiO_2$, and poisoning substances such as lead Pb and sulfur S are caught by alumina $Al_2O_3$, whereby the durability is improved.

In FIG. 3(d), the lamination order shown in FIG. 3(c) is reversed, and in FIGS. 3(e) and 3(f), a two-layer structure is given to the nitrogen oxide-reducing catalyst layer 43, and a layer of alumina $Al_2O_3$ is sandwiched as the protecting layer 44 between catalyst layers 43a and 43b.

As is apparent from the foregoing description, since a plate-shaped solid electrolyte is laminated on the substrate, a uniform catalyst reaction surface can be easily maintained and the reaction is uniformly advanced, and local degradation of the catalyst is not caused. These are effects attained by the present invention.

I claim:
1. An oxygen concentration-detecting apparatus for an internal combustion engine which comprises:
   a plate substrate;
   an oxygen ion-conducting solid plate electrolyte for generating an electromotive force between a first surface contacted with air and a second surface contacted with an exhaust gas of said engine according to the difference between the concentrations of oxygen gases of said air and said exhaust gas, said oxygen ion-conducting solid electrolyte being laminated on a surface of said substrate and said substrate restricting a cavity portion therebetween where air is introduced into;
   a pair of electrode members formed at said first and second surfaces, respectively, of said oxygen ion-conducting solid electrolyte, to take out said electromotive force as a detection signal; and
   a nitrogen oxide-reducing catalyst layer for promoting the reduction of nitrogen oxide disposed on said second surface of said oxygen ion-conducting solid electrolyte and said electrode located on said second surface.
2. An oxygen concentration-detecting apparatus as set forth in claim 1, wherein said nitrogen oxide-reduc- ing catalyst layer comprises at least rhodium supported on titanium oxide as the carrier.

3. An oxygen concentration-detecting apparatus as set forth in claim 1, wherein said nitrogen oxide-reducing catalyst layer includes a nitrogen oxide-reducing catalyst as well as an hydrocarbon and carbon monoxide oxidation catalyst.

4. An oxygen concentration-detecting apparatus as set forth in claim 3, wherein said oxidation catalyst comprises platinum supported on a carrier comprising alumina.

5. An oxygen concentration-detecting apparatus as set forth in claim 3, wherein said nitrogen oxide-reducing catalyst layer includes an oxidation catalyst layer as an auxiliary catalyst layer.

6. An oxygen concentration-detecting apparatus as set forth in claim 5, wherein said oxidation catalyst layer comprises platinum supported on a carrier comprising alumina.

7. An oxygen concentration-detecting apparatus as set forth in claim 1, which further comprises a protecting layer covering the outer side of said nitrogen oxide-reduction catalyst layer.

8. An oxygen concentration-detecting apparatus as set forth in claim 1, which further comprises a protecting layer arranged between said nitrogen oxide-reducing catalyst layer and said electrode located on said second surface of said oxygen ion-conducting solid electrolyte.

9. An oxygen concentration-detecting apparatus as set forth in claim 7, wherein said protecting layer comprises alumina and said nitrogen oxide-reducing catalyst layer comprises rhodium, ruthenium or iridium supported on titanium oxide.

10. An oxygen concentration-detecting apparatus as set forth in claim 8, wherein said protecting layer comprises alumina and said nitrogen oxide-reducing catalyst layer comprises rhodium, ruthenium or iridium supported on titanium oxide.

11. An oxygen cocentration-detecting apparatus as set forth in claim 1, which further comprises a heater integrally attached to said substrate.

12. An oxygen concentration-detecting apparatus for an internal combustion engine which comprises:
   a plate substrate;
   an oxygen ion-conducting solid plate electrolyte for generating an electromotive force between a first surface contacted with air and a second surface contacted with an exhaust gas of said engine according to the difference between the concentrations of oxygen gases of said air and said exhaust gas, said oxygen ion-conducting solid electrolyte laminated on a surface of said substrate and said substrate restricting a cavity portion therebetween where air is introduced into;
   a pair of electrode members formed at said first and second surfaces, respectively, of said oxygen ion-conducting solid electrolyte, to take out said electromotive force as a detection signal;
   an oxidation catalyst layer for promoting the oxidation reaction of hydrocarbon and carbon monoxide covering said second surface of said oxygen ion-conducting solid electrolyte and said electrode located on said second surface; and
   a nitrogen oxide-reducing catalyst layer for promoting the reduction reaction of nitrogen oxide covering said second surface of said oxygen ion-conducting solid electrolyte and said electrode located on said second surface.

13. An oxygen concentration-detecting apparatus as set forth in claim 2, wherein said nitrogen oxide-reducing catalyst layer is located on the outside of said oxidation catalyst layer.

14. An oxygen concentration-detecting apparatus as set forth in claim 12, wherein said oxidation catalyst layer is located on the outside of said nitrogen oxide-reducing catalyst layer.

15. An oxygen concentration-detecting apparatus as set forth in claim 12, which further comprises a protecting layer comprised of alumina covering said second surface of said oxygen ion-conducting solid electrolyte and said electrode located on said second surface.

16. An oxygen concentration-detecting apparatus as set forth in claim 15, wherein said protecting layer is located between said oxidation catalyst layer and said nitrogen oxide-reducing catalyst layer.

17. An oxygen concentration-detecting apparatus as set forth in claim 15, wherein said protecting layer is located between said oxygen ion-conducting solid electrolyte and any one of said oxidation catalyst layer and said nitrogen oxide-reducing catalyst layer.

18. An oxygen concentration-detecting apparatus as set forth in claim 12, which further comprises a heater integrally attached to said substrate.

* * * * *